United States Patent
Shellenberger

(10) Patent No.: US 11,778,975 B2
(45) Date of Patent: Oct. 10, 2023

(54) EDIBLE BEAN LINE <14451> (LUMEN)

(71) Applicant: Archer Daniels Midland Company, Decatur, IL (US)

(72) Inventor: Matthew Shellenberger, Caldwell, ID (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 16/785,540

(22) Filed: Feb. 7, 2020

(65) Prior Publication Data

US 2020/0253149 A1    Aug. 13, 2020

Related U.S. Application Data

(60) Provisional application No. 62/803,046, filed on Feb. 8, 2019.

(51) Int. Cl.
*A01H 6/54* (2018.01)
*A01H 5/10* (2018.01)

(52) U.S. Cl.
CPC ............... *A01H 6/545* (2018.05); *A01H 5/10* (2013.01)

(58) Field of Classification Search
None
See application file for complete search history.

(56) References Cited

U.S. PATENT DOCUMENTS

| | | | | |
|---|---|---|---|---|
| 8,558,077 B2 * | 10/2013 | Shellenberger | .......... | A01H 5/08 800/313 |
| 2020/0253148 A1 * | 8/2020 | Shellenberger | ........ | A01H 6/545 |

* cited by examiner

*Primary Examiner* — Cathy Kingdom Worley
(74) *Attorney, Agent, or Firm* — Andrew F. Nilles

(57) ABSTRACT

An edible bean seed designated as <14451> or LUMEN, a sample of the edible bean deposited under accession no. PI 698684 is disclosed. Methods of using the edible bean seed designated as <14451> or LUMEN for breeding new varieties of bean seed are also disclosed, as well as seeds of the edible bean seed designated as <14451> or LUMEN.

14 Claims, 1 Drawing Sheet

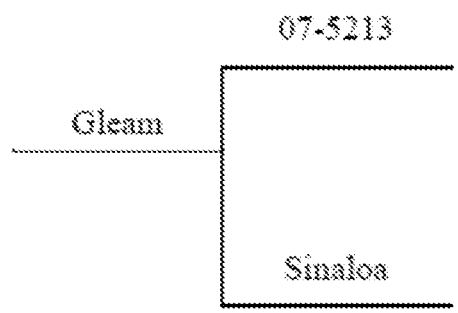

EDIBLE BEAN LINE <14451> (LUMEN)

CROSS-REFERENCE TO RELATED APPLICATIONS

This application claims the benefit under 35 U.S.C. § 119(e) of U.S. Provisional Application Ser. No. 62/803,046, filed Feb. 8, 2019, the contents of the entirety of which are incorporated by this reference.

TECHNICAL FIELD

The present invention relates generally to the field of plant breeding, and more specifically to edible bean line <14541> (LUMEN).

BACKGROUND OF THE INVENTION

In the United States, there is increasing concern over the consumption of high sugar and high fat foods by the population. An alarming increase in obesity among the citizens in the United States exists since many people in the United States are overweight due to a lack of exercise and poor eating habits.

Beans and peas are listed under both the Vegetables, and the Meats and Beans categories of the Dietary Guidelines Pyramid, thus, emphasizing the healthy nature of legumes in the diet. In addition to the emphasis on lower fat and lower sugar diets, beneficial effects of legumes are becoming apparent. Legumes are packed with fiber and protein, as well as being a good source of numerous vitamins and minerals. Legumes also have a low glycemic index and may help play a role in maintaining normal blood sugar levels; increasing digestive health; and even possibly improving heart health. Yet, legumes are an underutilized food in the United States diet.

With the increased awareness of the problems of obesity, poor eating habits, and the increased awareness of the health benefits of legumes, there exists a need for healthier food products and foodstuffs that provide the beneficial nutritional effects of legumes, as well as a consistent crop supply of such legumes.

SUMMARY OF THE INVENTION

In each of its various embodiments, the present invention helps fulfill these needs and discloses a pinto bean variety for use in breeding new bean varieties, as well as a foodstuff.

In one embodiment, an edible bean seed designated as LUMEN, a sample of the edible bean seed that was deposited under accession no. PI 698684, is disclosed.

In another embodiment, methods of using the edible bean seed LUMEN for breeding new varieties of bean seed are disclosed. Seeds of the edible bean seed designated as LUMEN are also disclosed.

BRIEF DESCRIPTION OF THE DRAWINGS

FIG. 1 shows the breeding history of edible bean line <14451> (LUMEN).

DETAILED DESCRIPTION OF THE INVENTION

In one embodiment, an edible bean line designated as <14451> or (LUMEN), is disclosed. As used herein, the term LUMEN will be used to refer to edible bean variety <14451>. Also disclosed are bean plants having the physiological and morphological characteristics of the edible bean line designated as LUMEN. Parts of the bean plant including, without limitation, pollen, ovules, pods and cells, as well as uses of such parts in breeding are further disclosed.

In another embodiment, seed of the edible bean line designated as LUMEN is disclosed. Such seed may be an essentially homogenous population of the edible bean line designated as LUMEN, wherein such seed of the edible bean line designated as LUMEN is essentially free of other seed. Accordingly, the seed of the present invention comprises at least 95% or more of seed of the edible bean line designated as LUMEN.

In yet a further embodiment, tissue culture of regenerable cells of the edible bean line designated as LUMEN are disclosed. Such tissue culture may be capable of expressing all of the physiological and morphological characteristics of the edible bean line designated as LUMEN, and be capable of regenerating plants having the same genotype of plants of the edible bean line designated as LUMEN. The tissue culture may be obtained from embryos, meristems, cotyledons, pollen, leaves, anthers, roots, root tips, pistil, flower, seed and/or stalks.

In an additional embodiment, breeding methods for producing edible bean seeds, plants and/or pods using the edible bean line designated as LUMEN of the present invention as a parent are disclosed. Such breeding methods may be used to prepare hybrid edible bean seed or plants or inbred edible bean seed or plants, where seed ultimately produced using the edible bean line designated as LUMEN as at least one of the parents are included within the scope of this invention.

In one embodiment, methods of crossing the edible bean line designated as LUMEN with itself of a second plant and the seeds and plants produced by such methods are disclosed. Such methods may be used for propagating edible bean line designated as LUMEN, or can be used to produce hybrid dry bean seeds and the plants grown therefrom.

In a further embodiment, the present invention discloses a process for producing beans comprising obtaining a plant of the edible bean line designated as LUMEN, cultivating the plant to maturity, and collecting and/or harvesting beans from the mature plant. Such beans may be used ultimately as a foodstuff, as seed or as parent in a breeding program.

The present invention further discloses methods and compositions relating to plants, seeds and derivatives of edible bean line designated as LUMEN. LUMEN has an erect growth habit, is indeterminate, has guides that are medium to long and has no ability to climb. LUMEN also has scattered pods that are not concentrated high or low, is adapted to machine harvest, and a good lodging resistance. LUMEN is a pinto bean variety exhibiting traits including, but not limited to carrying the recessive sd gene, such that LUMEN is slow darkening as compared to other pinto bean lines. LUMEN will retain a bright, white color through adverse weather conditions or when being stored. Observations and seed increase show that edible bean line designated as LUMEN shows uniformity and stability, without variants.

Origin and Breeding History.

The development of the edible bean line designated as LUMEN can be summarized as follows. A cross was made between pinto variety 'Sinaloa' as the male parent and the ProVita pinto variety '07-5213' as the female parent. The cross was made during the spring in Year 1 in the greenhouse. The edible bean line designated as LUMEN was derived from this cross.

The breeding history of edible bean line designated as LUMEN is shown in FIG. 1.

TABLE 1

The following Table indicates the selections used to produce the edible bean line designated as LUMEN.

| Year | Location | Generation | Bulk (lbs) | Single Plant Selections |
|---|---|---|---|---|
| Summer Year 1 | Twin Falls, ID-field | F1 | <3 lb | |
| Summer Year 2 | Twin Falls, ID-field | F2 | <3 lbs | |
| Summer Year 3 | Twin Falls, ID-field | F3 | | 5 single plant selections |
| Summer Year 4 | Twin Falls, ID-field | F4 | | 2 single plant selections |
| Summer Year 5 | Twin Falls, ID-field | F5 | | 2 single plant selections |
| Summer Year 6 | Twin Falls, ID-field | F6 | <3 lbs | |
| Summer Year 7 | Twin Falls, ID-field | F7 | <3 lbs | |
| Summer Year 8 | Nampa, ID-field | F8 | 140 lbs | |
| Summer Year 9 | Nampa, ID-field | F9 | 3300 lbs | |
| Summer Year 10 | Idaho-Field | F9 | | Seed Production for Trials and Stocks |
| Summer Year 11 | Idaho-Field | F10 | | Seed Production for Trials and Stocks |

Selections were done in the F3, F4, and F5 generations as follows. In the F3 generation, there was segregation for architecture, maturity, seed gloss, seed color, and seed size. Single plant selections were made for upright architecture, high pod set, yield, seed gloss, seed color, seed size, and acceptable maturity. In the F4 generation, single plant selections were made for upright architecture, high pod set, yield, seed color, seed size, and acceptable maturity. In the F5 generation, single plant selections were made for upright architecture, high pod set, yield, seed color, seed size, and acceptable maturity. Such selections resulted in the new edible bean line designated as LUMEN, which was observed to be uniform, stable, and substantially free of any variants within commercially acceptable limits since the F6 generation. It is known that a small percentage of off-types may occur for a characteristic of edible bean line designated as LUMEN during multiplication.

Physiological and Morphological Characteristics of Edible Bean Line Designated as LUMEN.

Table 2 depicts the physiological and morphological characteristics of edible bean line designated as LUMEN.

TABLE 2

| Characteristic | Edible bean line designated as LUMEN |
|---|---|
| Market Class | Pinto |
| Maturity | Medium (90-100 days) |
| Days from planting to harvest maturity | 94 |
| Plant Habit | |
| Type | Erect growth habit-indeterminate, guides medium to long with no ability to climb |
| Average height of mature plant | Not measured |
| Pod position | Scattered (not concentrated high or low) |
| Adaptability to machine harvest | Adapted |
| Lodging resistance | Good |
| Leaflet morphology | |
| Leaflet Shape | Not determined Ovate |
| Apex of leaflet | Acuminate |
| Base of leaflet | Obtuse |
| Flower color and days to bloom | |
| Color of standard | Not determined |
| Color of wings | Not determined |
| Color of keel | Not determined |
| Days to 50% bloom | 44 |
| Pod Morphology | |
| Green color pattern | Not determined |
| Mature color pattern | Not determined |
| Green primary color | Not determined |
| Mature primary color | Not determined |
| Green color modifier | Not determined |
| Mature color modifier | Not determined |
| Green secondary color | Not determined |
| Mature secondary color | Not determined |
| Green cross section shape | Not determined |
| Mature cross section shape | Not determined |
| Green pod curvature | Not determined |
| Mature pod curvature | Not determined |
| Green pod beak orientation | Not determined |
| Mature pod beak orientation | Not determined |
| Green constrictions | Slight |
| Mature constrictions | Slight |
| Average number of seeds/pod | Not determined |
| Seed Color | Semishiny and polychrome |
| Primary color | Buff |
| Secondary color | Brown |
| Color pattern | Mottled |
| Hilar ring | Present |
| Hilar ring color | Yellow |
| Seed Shape and Weight | |
| Shape of seed taken from middle of pod | Cuboid |
| Dry seed weight in g/100 g Seeds (adjusted to 12% moisture) | 39 |
| Anthocyanin Pigmentation* | |
| Flowers | Not determined |
| Leaves | Not determined |
| Stems | Not determined |
| Petioles | Not determined |
| Pods | Present |
| Peduncles | Not determined |
| Seeds | Present |
| Nodes | Not determined |
| Known Disease Resistance | Intermediate resistance to bean rust (Uromyces appendiculatus) Resistant to bean common mosaic virus (BCMV), NL8 |

LUMEN carries the recessive sd gene that confers resistance to darkening due to age or environmental conditions. This slow darkening gene is a particular benefit to pinto bean crops that are grown in environments that darken traditional pinto beans. LUMEN will retain improved bright white color through adverse weather conditions or when being stored.

DEPOSIT INFORMATION

A deposit of the edible bean line designated as LUMEN of the present invention will be made with the National Center for Genetic Resources Preservation, 1111 S. Mason St., Fort Collins, Colo. The date of deposit is Jun. 23, 2021. Upon issuance of a patent, all restrictions upon the deposit will be removed, and the deposit is intended to meet all of the requirements of 37 C.F.R. § 1.801-1.809. The accession number for the deposited seeds of edible bean line designated as LUMEN is PI 698684. The deposit will be maintained in the depository for a period of 30 years, or 5 years after the last request, or for the enforceable life of the patent, whichever is longer, and will be replaced if necessary during such period.

The present invention has been described with reference to certain exemplary embodiments, legume products, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. An edible bean seed designated as LUMEN, a sample of the edible bean seed deposited under accession no. PI 698684.

2. A plant, or parts thereof, produced by growing the edible bean seed of claim 1.

3. Pollen of the plant of claim 2.

4. An edible bean plant having all of the physiological and morphological characteristics of the edible bean plant of claim 2.

5. A tissue culture of regenerable cells of the edible bean plant of claim 2.

6. The tissue culture of claim 5, wherein the cells are obtained from a plant part selected from the group consisting of leaf, pollen, embryo, meristematic cell, root, root tip, anther, stomatal cell, flower, seed, stem, pod and combinations of any thereof.

7. An edible bean plant regenerated from the tissue culture of claim 6, having all of the morphological and physiological characteristics of an edible bean plant grown from an edible bean seed designated as LUMEN, a sample of the edible bean seed deposited under accession no. PI 698684.

8. A method for producing an edible bean seed comprising crossing two edible bean plants and harvesting the resulting edible bean seed, wherein at least one of the two edible bean plants is the edible bean plant of claim 2.

9. A method for producing a hybrid edible bean seed comprising crossing the edible bean plant of claim 2 with a second edible bean plant and harvesting the resulting hybrid edible bean seed.

10. A plurality of the edible bean seeds of claim 1.

11. A method of planting a field, comprising planting the plurality of the edible bean seeds of claim 10 in the field.

12. A process for producing edible beans for consumption, comprising processing the plurality of the edible bean seeds of claim 10 such that the plurality of the edible bean seeds are suitable for consumption.

13. A method for producing an edible bean seed designated as a LUMEN-derived edible bean seed, the method comprising:

crossing a plant of edible bean seed designated as LUMEN, a sample of the seed deposited under accession number PI 698684, with a second edible bean plant to yield progeny edible bean seed; and growing the progeny edible bean seed to yield LUMEN-derived edible bean plants and allowing seed of LUMEN-derived edible beans plants to form.

14. The method of claim 13, wherein the second edible bean plant is transgenic.

* * * * *